United States Patent [19]

Konopa

[11] Patent Number: 5,292,527
[45] Date of Patent: Mar. 8, 1994

[54] NON-ALCOHOLIC AQUEOUS MOUTHWASH

[75] Inventor: Kenneth D. Konopa, Duluth, Ga.

[73] Assignee: Bausch & Lomb Incorporated, Rochester, N.Y.

[21] Appl. No.: 908,091

[22] Filed: Jul. 2, 1992

[51] Int. Cl.⁵ .......................... A61K 7/16; A61K 7/22; A61K 7/26
[52] U.S. Cl. ........................ 424/54; 424/49; 424/58
[58] Field of Search ..................... 424/49-58

[56] References Cited

U.S. PATENT DOCUMENTS

| | | | |
|---|---|---|---|
| 3,639,563 | 2/1972 | Januszewski | 424/49 |
| 3,947,570 | 3/1976 | Pensak et al. | 424/51 |
| 4,096,241 | 6/1978 | Geistlich et al. | 424/54 |
| 4,132,770 | 1/1979 | Barth | 424/49 |
| 4,420,471 | 12/1983 | Elton et al. | 424/49 |
| 4,465,661 | 8/1984 | Schmolka II | 424/49 |
| 4,476,107 | 10/1984 | Schmolka I | 424/49 |
| 4,522,806 | 6/1988 | Muhlemann et al. | 424/52 |
| 4,670,185 | 6/1987 | Fujiwara et al. | 252/311 |
| 4,689,214 | 8/1987 | Niles et al. | 424/49 |
| 4,765,984 | 8/1988 | Vellekoop et al. | 424/441 |
| 4,828,822 | 5/1989 | Muhlemann et al. | 424/52 |
| 4,919,918 | 4/1990 | Cole et al. | 424/44 |
| 4,923,685 | 5/1990 | Wuelknitz et al. | 424/54 |
| 4,945,087 | 7/1990 | Tazwar et al. | 514/60 |
| 4,971,785 | 11/1990 | Wilson et al. | 424/44 |
| 4,976,954 | 11/1990 | Kleber et al. | 424/49 |
| 4,992,259 | 2/1991 | Schiraldi et al. | 424/49 |
| 4,992,276 | 2/1991 | Dills et al. | 424/439 |
| 5,035,881 | 7/1991 | Mori et al. | 424/54 |
| 5,078,988 | 1/1992 | Lin et al. | 424/49 |
| 5,087,444 | 2/1992 | Jackson et al. | 424/49 |
| 5,100,650 | 3/1992 | Carlin et al. | 424/49 |
| 5,108,735 | 4/1992 | Ohtsukl et al. | 424/50 |
| 5,112,600 | 5/1992 | Jackson et al. | 424/55 |
| 5,130,122 | 7/1992 | Tabibi et al. | 424/49 |
| 5,145,664 | 9/1992 | Thompson | 424/49 |
| 5,154,915 | 10/1992 | Weber et al. | 424/54 |
| 5,182,101 | 1/1993 | Wuelknitz et al. | 424/54 |
| 5,211,940 | 5/1993 | Ishiguro et al. | 424/49 |

Primary Examiner—Shep K. Rose
Attorney, Agent, or Firm—Denis A. Polyn; James B. Bieber

[57] ABSTRACT

A non-alcoholic, aqueous mouthwash composition is provided which contains a dispersion system containing a non-ionic surfactant selected from an hydrogenated castor oil and a polyoxyethylene polyoxypropylene block copolymer having about 50% to about 90% ethylene oxide, a humectant and a cationic antimicrobial agent. The composition exhibits a homogeneous, uniform appearance and a high degree of bacterial efficacy.

22 Claims, No Drawings

NON-ALCOHOLIC AQUEOUS MOUTHWASH

BACKGROUND OF THE INVENTION

1. Field of the Invention

This invention relates to a non-alcoholic, aqueous mouthwash composition. More particularly, the present invention relates to a non-alcoholic mouthwash composition which exhibits a homogeneous, uniform appearance and a high degree of bactericidal efficacy.

2. Description of the Art

Mouthwashes and oral rinse compositions have been used for many years and the art is replete with various compositions and formulations. Ordinarily, mouthwashes have been designed to clean the oral cavity, provide fresh breath and kill harmful bacteria. It is generally necessary to kill certain oral bacteria that contribute to malodor or secrete acidic residues which are harmful to teeth and aid in the development of gingivitis and periodontal disease.

Conventional mouthwashes contain a fairly high percentage of ethyl alcohol ranging from 10% to 30% by weight of the total composition. This alcohol is used both as a disinfectant and as a solvent in which other additives such as flavoring oils, color additives, fluorides and astringents can be dissolved and then dispersed into the aqueous solution. In fact, more than 95% of commercial mouthwash compositions contain greater that 15% by weight alcohol. These high concentrations of ethyl alcohol are primarily used to kill oral bacteria since lower concentrations are generally adequate to disperse the additives into the aqueous solution.

However, the use of alcohol in mouthwash compositions has detrimental or undesirable side effects for many user groups. For example, many people cannot tolerate alcohol and must, for medical and health reasons, avoid the use of mouthwash compositions containing alcohol. Further, young children and persons over the age of sixty are extremely susceptible to health risks when ingesting large quantities of alcohol. Generally, recovering alcoholics must avoid oral contact with alcohol as well as persons of certain religious beliefs. Last, those persons afflicted by dry-mouth syndrome or using certain medications, often prefer to avoid alcohol containing mouthwash compositions since the alcohol tends to remove moisture from the oral tissues and complicate the dry-mouth syndrome or feeling.

Various attempts have been made at developing non-alcoholic mouthwashes. For example, U.S. Pat. No. 4,919,918 to Cole et al and U.S. Pat. No. 4,971,785 to Wilson et al are directed to a non-alcoholic delivery system which can be used in mouthwashes. However, these patents are primarily directed to dry compositions which are dissolved in water immediately prior to use. Dry compositions avoid some of the problems associated with alcohol-free aqueous compositions, namely the inability of the aqueous compositions to form homogeneous and stable products.

While there is clearly a need for a non-alcoholic mouthwash, there are few aqueous, non-alcoholic mouthwashes in ready-to-use form commercially available which can achieve acceptable bactericidal efficacy. One commercial alcohol-free mouthwash is sold under the trademark AL-FREE by Keystone Research and Pharmaceutical, Inc. of Cherry Hill, N.J. This product contains water, glycerin, propylene glycol, polysorbate 20 and 80, cetyl-pyridinium chloride, flavors, sweeteners, and coloring agents. However, this product does not exhibit a high level of bactericidal efficacy.

While surfactants would normally be employed to achieve dispersion of the water insoluble additives, their use is limited in the present application. The use of various surfactants or surface active agents to achieve and maintain sufficient dispersion of the water insoluble components, particularly the flavoring oil, have been found to inhibit the activity of certain antimicrobial agents. Since the use of surfactants is deleterious to the activity of certain antimicrobial agents and thus, to achieving acceptable bactericidal efficacy, there are currently no known commercially available, ready-to-use alcohol-free, aqueous mouthwashes which effectively kill harmful microorganisms.

Accordingly, a significant problem encountered with formulating an alcohol-free mouthwash is that while the use of surfactants are necessary to achieve proper dispersion, these surfactants typically inhibit the activity of the antimicrobial agent. Thus, an alcohol-free mouthwash must have the ability to achieve sufficient bactericidal efficacy while obtaining complete dispersion of the water insoluble components in the aqueous composition. The present invention addresses this problem by the use of a specific dispersion system which results in a stable, homogeneous composition with good bactericidal efficacy. More specifically, it has been surprisingly found that certain surfactants, when used in low concentrations, can provide the necessary dispersing and stability characteristics needed in alcohol-free systems and also which do not adversely affect the activity of the antimicrobial agent employed.

SUMMARY OF THE INVENTION

According to this invention, an aqueous, non-alcoholic mouthwash composition is provided which contains a water-insoluble flavoring oil and an effective amount of a dispersion system comprising a non-ionic surfactant selected from a hydrogenated castor oil and a polyoxyethylene polypropylene block copolymer having about 50% to 90% ethylene oxide, a humectant, and a disinfecting amount of a least one cationic antimicrobial agent, and wherein the composition has a homogeneous, uniformed appearance.

Also provided herein is a method for preparing an aqueous, non-alcoholic mouthwash composition wherein the surfactant is hydrogenated castor oil present in an amount of less than about 1.0% by weight of the total composition comprising:

a) mixing a water-insoluble flavoring oil into a hydrogenated castor oil surfactant to form a mixture;

b) adding a humectant to said mixture to form a first phase;

c) mixing an antimicrobial agent into water to form a second phase, and;

d) mixing the first phase into the second phase in a slow, controlled manner so as to prevent the first phase from visually coagulating into discrete particles in the second phase.

DETAILED DESCRIPTION OF THE INVENTION

The present invention is an aqueous, non-alcoholic mouthwash which is intended to be used in place of alcohol-containing preparations. The present mouthwash composition contains a water insoluble flavoring oil and an effective amount of a dispersion system composed of a non-ionic surfactant selected from either a hydrogenated castor oil surfactant or a polyoxyethylene polyoxypropylene block copolymer having about 50% to 90% ethylene oxide, a humectant, and an effective amount of one or more cationic antimicrobial agents.

The water-insoluble flavoring oil component can be any of the available well known essential oils which are suitable for use in mouthwash compositions. Typically, the flavoring oils may be chosen from synthetic flavor oils, flavoring aromatics, oleo resins and extracts derived from plants and the like, and combinations thereof. Illustrative examples of such flavoring oils include spearmint oil, cinnamon oil, oil of wintergreen (methyl salicylate), peppermint oil, clove oil, bay oil, eucalyptus oil, thyme oil, cedar leaf oil, oil of nutmeg, oil of sage, oil of bitter almonds and the like. Commonly used flavoring oils also include mints, such as peppermint, menthol, various fruit flavors, and cinnamon derivatives. Moreover, flavorings such as aldehydes and esters can also be used.

The amount of flavoring oils employed is normally dependent on a number of variables such as the flavor desired, the flavoring ingredient used, and the organoleptic strength desired. Accordingly, the amount may be varied within the capabilities of those skilled in the art. Typically, the flavoring oils are used in amounts from about 0.05% to about 2.0% by weight of the final composition.

The hydrogenated castor oil surfactants are known non-ionic solubilizing and emulsifying agents. These products are produced by allowing hydrogenated castor oil to react with ethylene oxide. Particularly known surfactants are the products sold under the trademark CREMOPHOR RH by BASF Corp. of Parsippany, N.J. The main constituents of these products are esters of hydrogenated castor oil fatty acids with oxyethylated glycerol. In addition, they may contain polyglycol esters of the hydrogenated castor oil fatty acids and may also include free oxyethylated glycerol and higher polyethylene glycols. The fatty acid esters of the glycerol polyethylene glycol and fatty acid esters of polyethylene glycol represent the hydrophobic part of the products. The hydrophilic part of the products are the polyethylene glycols and ethoxylated glycerol. The preferred CREMOPHOR products are sold under the designations RH40 which has a saponification value of 50 to 60 and a hydroxyl value of 60 to 75, RH410 with a saponification value of 45 to 55 and no significant hydroxyl value, RH455 with a saponification value of 45 to 55 and no significant hydroxyl value, and RH60 with a saponification value of 40 to 50 and a hydroxyl value of 50 to 70. Most preferred is the RH grade 40.

The polyoxyethylene polyoxypropylene block copolymers are known as poloxamer polyols and are non-ionic. The polyols comprise a central lipophilic molecule (polyoxypropylene moiety) surrounded by sequences of hydrophiles (oxyethylene moiety). Chemically, these copolymers can be classified like those of polyethers or those of ether alcohols. These copolymers are represented by the formula:

$$HO(C_2H_4O)b(C_3H_6O)a(C_2H_4O)bH \qquad (I)$$

wherein a is a number which represents the moles of the lipophilic base such that it has a molecular weight of about 2800 to about 4000, and b is a number wherein 2xb equals the number of moles of the hydrophilic portion which constitutes about 70% to about 90% by weight of the copolymer. Preferably, the copolymers or poloxamer polyols are of the solid type. Examples of suitable copolymers or poloxamer polyols of the solid type are PLURONIC F88, F98, F108 and F127 sold by BASF corp. of Parsippany, N.J. These copolymers contain a lipophilic moiety of molecular weight of about 2800 to about 4000 and a hydrophilic moiety of about 50% to 80% by weight of the copolymer. The most preferred solubilizing agent is PLURONIC 108, with a molecular weight of about 15,000. The letters and numbers of each PLURONIC copolymer identify and characterize the polyol. The letter indicates the physical nature of the product. (i.e. L=liquid, P=paste, F=solid). The last digit of the number multiplied by 10 represents the percentage of the part of the hydrophile in the final copolymer. The first and second digit (in the case of a three-digit number) indicates the importance of the lipophilic part of the copolymer. For example, the preferred copolymer, PLURONIC F108, indicates a solid body composed of about 80% ethylene oxide and a one sequence lipophile molecular weight of about 3300.

The surfactant component is used in combination with a suitable humectant. Examples of suitable humectants include glycerin, sorbitol, and mannitol with glycerin being preferred. A suitable amount of humectants are employed to ensure that the final composition has the desired degree of moistening mouth feel. Generally, the humectant is present in amounts from about 1.0% to 20% by weight of the final composition.

The dispersion system employed in the present invention also includes a disinfecting amount of one or more cationic antimicrobial agents. The antimicrobial agents used herein are known in the art and include cetylpyridinium chloride (CPC) and other quaternium ammonium salts used in oral applications, domiphen bromide and combinations thereof. The preferred antimicrobial agent is capable of aiding the dispersion of the water-insoluble flavoring oil in the aqueous medium while still providing suitable antimicrobial efficacy at low concentrations. The preferred antimicrobial agent is a combination of CPC and domiphen bromide in ratios of about lo to 50 parts CPC per part domiphen bromide. The antimicrobial agents used herein are present in low concentrations from about 0.002% to about 0.2% by weight of the final composition.

It is important that the non-ionic surfactant employed herein be used in low concentrations so as not to inhibit the activity of the antimicrobial agent. It has been surprisingly found that the present surfactants used in amounts of less than about 1.0% and, most preferably, in amounts of not more than 0.6% by weight of the final composition can achieve the desired dispersion and stability characteristics without adversely affecting the activity of the antimicrobial agent employed. However, when the present surfactants are used in higher concentrations, the activity of the antimicrobial agent is reduced. Generally, the ratio of antimicrobial agent to surfactant is preferably from about 1 part antimicrobial agent to about 1 to 500 parts surfactant.

Surprisingly, other surfactants commonly used in oral compositions, particularly non-ionic surfactants, do not appear to be able to achieve the desired dispersion characteristics without adversely inhibiting the activity of the antimicrobial agent employed. For example, as shown below, certain polysorbitols (TWEENS) have a neutralizing or deactivating affect on the antimicrobial agents which render the compositions less effective at killing the harmful microorganisms. Anionic surfactants are also believe to adversely affect the cationic antimicrobial agents.

The mouthwash compositions of the present invention generally have pH within the range of 5.0 to 7.0. It is preferred that the pH of the system be slightly acidic such as between 5.5 to 6.5. A suitable buffer is employed to ensure that the final composition stays within this pH range. Any of the well known buffers used in oral care compositions can be employed. Illustrative examples of suitable buffers include alkali metal salts, preferably sodium salts, such as sodium phosphate, sodium benzoate, sodium borate, sodium citrate, sodium phosphate and the like with sodium phosphate monobasic and sodium phosphate dibasic or combinations thereof being most preferred. The buffers are generally used in amounts necessary to obtain and maintain the pH level described above. Typically, the buffers are present in amounts from about 0.1% to 1.0% by weight of the final composition.

The sweetness of the composition can be adjusted using any of the conventional sweetening agents used in oral care applications. Examples of suitable sweetening agents include sugars such as monosaccharides and disaccharides and artificial sweeteners such as saccharin salts, cyclamate salts, acesulfame-K, aspartame and its derivatives, and the like. Typically, these sweeteners will be present in amounts from about 0.01% to about 2.0% by weight of the final composition depending on the specific sweetener employed. Preferred are the saccharin salts such as sodium saccharin, used in amounts from 0.05% to 0.1% by weight of the final composition.

Various coloring agents may also be employed in effective amounts to produce the desired colors. The coloring agents may include natural food colors and dyes suitable in oral care compositions and are preferably water-soluble. These colorings are generally known as FD&C dyes. Preferred are the water soluble blues, yellows, greens and reds such as FD&C Blue #1, FD&C Yellow #5, FD&C Green #3, and FD&C Red #3.

Finally, the present invention may also contain various other components which do not inhibit the effectiveness of the dispersion system or the bactericidal efficacy of the composition. Examples of such components include, but are not limited to, fluorides, preservatives, chelating agents and the like.

The composition of the present invention is alcohol-free and no alcohol per se is added to the present composition. By alcohol free, it is meant that there will be less that 0.1% alcohol present and preferably less than about 0.01% alcohol present in the final composition. The presence of small or trace amounts of alcohols can result from the particular flavoring oil selected which by their nature or their manufacture contains trace amounts of alcohol.

The compositions of the present invention have a clear, homogeneous and uniform appearance and are stable under normal storage and shipping conditions. Most importantly, these compositions do not have visually noticeable particulates or oil suspensions floating on or in the aqueous medium. Typically, these compositions exhibit shelf stability at room temperature for more than a year. Further, the mouthwash compositions of this invention have been shown to be highly stable in accelerated stability tests. For example, the compositions tested exhibited no visible separation at three months in a constant environment of 37° C.

Under normal use, these compositions are contacted with the oral cavity for between five and sixty seconds although longer periods can be employed.

It has also been found that the dispersion system of the present composition exhibits a high degree of bactericidal efficacy. Most conventional mouthwashes rely substantially on the alcohol component in the composition to kill the harmful microorganisms. However, the present compositions achieve generally comparable bactericidal efficacy in the absence of ethyl alcohol.

As mentioned above, disinfecting amounts of an antimicrobial are used in the present invention. As used herein "a disinfecting amount" of an antimicrobial agent is an amount which will reduce a microorganism population comprising a mixture of *candida albicans, escherichia coli,* and *stapohylococcus aureus* by at least one log order in one minute. In one embodiment of this invention, a combination of CPC and domiphen bromide used with 0.6% of PLURONIC 108 has exhibited at least three log reductions of a mixture of these microorganisms in three minutes.

The present compositions employing hydrogenated castor oil surfactants are prepared according to the following process and are manufactured using conventional mixing equipment and vessels. The individual components are mixed in two separate phases and the phases are added together to produce the final compositions. The first phase consists of the buffer salts, sweeteners, and the antimicrobial agent(s). The second phase consists of the hydrogenated castor oil surfactants, the water-insoluble flavoring oils, and the humectant. The order in which the ingredients are mixed in the first phase is not critical. However, in the second phase, the water-insoluble flavoring oil is first dispersed into the hydrogenated castor oil surfactant and then the humectant is added to the mixture. Once the phases are well mixed, the second phase is slowly added to the first phase. Typically, the second phase is added to the first phase at a rate of about four to about eight gallons per minute in order prevent the second phase from visually coagulating into white particles which render the mixture cloudy.

The present compositions employing polyoxyethylene polyoxypropylene block copolymers are prepared using the same process except the water from the first phase can be added directly to the completed second phase and the salts are added thereafter in a single processing vessel.

The present invention is further illustrated by the following examples.

Examples 1–5 were prepared with the composition as shown in Table 1.

TABLE 1

| | (g/100 ml) | | | | |
|---|---|---|---|---|---|
| | 1 | 2 | 3 | 4 | 5 |
| CREMOPHOR RH40 | .6 | — | — | .6 | — |
| TWEEN 20 | — | .6 | — | — | — |
| PLURONIC 108 | — | — | .6 | — | — |
| Sodiumlauryl Sulfate | — | — | — | .1 | — |
| Flavoring Oil | .2 | .2 | .2 | .2 | .2 |
| Glycerin Water | 10.0 | 10.0 | 10.0 | 10.0 | 10.0 |
| Sodium Monophosphate | .41 | .41 | .41 | .41 | .41 |
| Sodium Diphosphate | .11 | .11 | .11 | .11 | .11 |
| Sodium Saccharin | .07 | .07 | .07 | .07 | .07 |
| CPC | .1 | .1 | .1 | .1 | .1 |
| Domiphen Bromide | .005 | .005 | .005 | .005 | .005 |
| FD + C Blue #1 | .0005 | .0005 | .0005 | .0005 | .0005 |

TABLE 1-continued

| | (g/100 ml) | | | | |
|---|---|---|---|---|---|
| | 1 | 2 | 3 | 4 | 5 |
| D + C Yellow #10 | .0005 | .0005 | .0005 | .0005 | .0005 |

Examples 1, 2 and 4 were 2 phase additions. Phase 1 was prepared by mixing the flavoring oil and surfactant components together in an emulsion. Glycerin was then added to the emulsion with rigorous mixing. Phase 2 was prepared by adding the rest of the various salts, sweetening agents, antimicrobial agents and color agents to a predetermined amount of water. Phase 1 was then slowly added to phase 2 with rigorous mixing for about 30 minutes.

Example 3 was also a two phase addition. However, the PLURONIC surfactant was first diluted into a 10% aqueous solution. Phase 1 was prepared by adding the PLURONIC surfactant to water (in a 1:10 ratio) with rigorous mixing and heating to a temperature of about 60° C. When the PLURONIC was completely dissolved, heating was discontinued and the solution was cooled to 25° C. The flavoring oil was added to the cooled solution with vigorous mixing to form an emulsion. Glycerin was then added to the emulsion with vigorous mixing. Phase 2 was prepared in the same manner as in the other examples and phase 1 was added to phase 2 with vigorous mixing.

Example 5 contains no surfactant. Phase 1 consisted of the flavoring oil and glycerin components mixed together. Phase 2 was prepared in the same manner as in the examples above and phase 1 was added to phase 2 with vigorous mixing.

Each composition was then tested for its ability to kill a mixture of microorganisms according to the following procedure. A simulated use mouthwash biocidal screen was performed on Examples 1–5 using sterile fetal calf serum (FCS) as the organic soil. Determination of the kill rates of three opportunistic oral pathogens; $s.$ $aureus$, $e.$ $coli$ and $c.$ $albicans$, was measured after one and three minute time exposures. The oral pathogens were prepared individually at about $2 \times 10^8$ colony forming units per ml (CFU ml) in phosphate buffered saline solution. An aliquot of 0.1 ml of each was added to a single centrifuge tube and diluted with 25 ml of FCS to target a final concentration of about $1 \times 10^6$ CFU/ml for each organism. A 1.0 ml aliquot of microbe/FCS was added to 20 ml of mouthwash or control solution contained in a 50 ml polypropylene tube. The tubes were agitated for five to ten seconds after initial inoculation and then agitated again for approximately an additional five seconds prior to sampling at one minute and three minutes time points. After one and three minutes exposure, 0.5 ml of the inoculated mouthwash composition was added to a primary neutralization tube of Dey-Engley broth (DEB). Further DEB dilutions and plates were made from the primary DEB tube. All plates and broth tubes were incubated aerobically at 30°–35° C. for twenty-four hours, and at room temperature (20°–25° C.) for an additional forty-eight to seventy-two hours.

Plate counts were then determined to calculate reduction in CFU/ml for the organisms. The calculated log order reductions for each composition is shown in Table 2.

| Example | Surfactant (g/100 ml) | Log Reduction in 1 minute | Log Reduction in 3 minutes | Visual Appearance |
|---|---|---|---|---|
| 1. | 0.6% CREMOPHOR | <1 | 1.7 | Homogeneous appearance |
| 2. | 0.6% polysorbital (TWEEN 20) | 1.0 | 2.0 | Homogeneous appearance |
| 3. | 0.6% PLURONIC 108 | 2.0 | 5.0 | Homogeneous appearance |
| 5. | No surfactant | 2.5 | 5.4 | Separate phases |
| 4. | 0.1% sodium lauryl sulphate + CHREMOPHOR RH40 | <1 | <1 | Separate phases |

Examples 6–15 were prepared as described above with the same amounts of flavoring oil, glycerin, sodium monophosphate, sodium diphosphate, sodium sacchrin, CPC, domiphen bromide, and coloring agents with various amounts of surfactants as shown in Table 3. Sufficient water was added to each composition to equal 100%.

Examples 6–15 were tested for their ability to kill a mixture of microorganisms using the procedure described above. The results are also shown in Table 3.

TABLE 3 *

| | 6 | 7 | 8 | 9 | 10 | 11 | 12 | 13 | 14 | 15 |
|---|---|---|---|---|---|---|---|---|---|---|
| PLURONIC 108 | — | — | — | — | — | 1.2 | 0.95 | 0.6 | 0.45 | — |
| PLURONIC F127 | — | — | — | — | — | — | — | — | — | 0.6 |
| CREMOPHOR RH40 | 1.2 | 0.95 | 0.6 | 0.45 | — | — | — | — | — | — |
| CREMOPHOR RH60 | — | — | — | — | 0.6 | — | — | — | — | — |
| Log Reductions after 1 min. | 0.5 | 0.5 | 0.8 | 0.9 | 0.8 | 0.6 | 0.6 | 0.7 | 1.1 | 0.8 |
| Log Reductions after 3 min. | 1.7 | 1.9 | 3.3 | 3.7 | 2.6 | 0.5 | 1.0 | 2.0 | 2.8 | 2.2 |

* All compositions exhibited a homogeneous appearance

It is to be understood that the subject invention is not to be limited to the above examples which have been provided to demonstrate operability of the invention. The scope of the invention shall include equivalent embodiments, modifications, and variations that fall within the scope of the attached claims.

What is claimed is:

1. An aqueous, slightly acidic, non-alcoholic mouthwash composition made by a method, comprising:
   a) mixing a water insoluble flavoring oil in an amount of about 0.05 to about 2.0% by weight of said composition into a hydrogenated castor oil surfactant in an amount of less than about 1.0% by weight of said composition to form a mixture;
   b) adding, subsequently, a humectant to said mixture in an amount sufficient to form a first phase that is clear and homogeneous in appearance;
   c) mixing at least one cationic antimicrobial agent into water that comprises about 0.1% to about 1.0% by weight of said composition of a buffer effective to obtain a slightly acidic final pH to form a second phase; and
   d) mixing said first phase into said second phase in a slow, controller manner so as to prevent said first phase from visually coagulating into discrete particles in said second phase wherein said mixed composition is of clear, homogeneous, stable appearance.

2. The composition of claim 1 wherein said antimicrobial agent is a combination of cetylpyridinium chloride and domiphen bromide.

3. The composition of claim 1 wherein said humectant is selected from the group consisting of glycerin, sorbitol, and mannitol.

4. The composition of claim 3 wherein said humectant is glycerin.

5. The composition of claim 1 wherein said hydrogenated castor oil has a saponification value of 45 to 55 and no significant hydroxyl value.

6. The composition of claim 5 wherein said hydrogenated castor oil is present in amounts of not more than 0.6% by weight.

7. The composition of claim 1 further comprising a sweetening and a coloring agent.

8. The composition of claim 1 wherein said composition can reduce the population of $s.$ $aureus,$ $e.$ $coli$ and $c.$ $albicans$ by about three log orders after three minutes of exposure.

9. The composition of claim 1 wherein said composition does not exhibit any visual separation after three months at a constant temperature of 37° C.

10. The non-alcoholic aqueous mouthwash composition of claim 15 comprising from about 70% to about 95% water, about 0.1% to about 3.0% of a water insoluble flavoring oil, about 0.1% to about 1.0% of a surfactant that is a hydrogenated castor oil, about 1.0% to 20.0% of a humectant, and a disinfecting amount of at least one cationic antimicrobial agent wherein the ratio of antimicrobial agent to surfactant is 1 part antimicrobial agent to 1 to 500 parts surfactant and wherein said composition has a homogeneous, uniform appearance.

11. The composition of claim 10 wherein said antimicrobial agent is a combination of cetylpyridinium chloride and domiphen bromide.

12. The composition of claim 10 wherein said surfactant is present in amounts of not more than 0.6% by weight.

13. A method for reducing the population of microorganisms selected from $s.$ $aureus,$ $e.$ $coli$ and $c.$ $albicans$ found in a mammalian oral cavity comprising contacting said oral cavity with the composition of claim 1.

14. The method of claim 13 where said composition is in contact with said oral cavity for a period of five to sixty seconds.

15. The method of claim 13 wherein the ratio of said surfactant to said antimicrobial agent is one part surfactant to 1 to 200 parts antimicrobial agent.

16. The method of claim 14 wherein said reduction is at least one log order.

17. A non-alcoholic slightly acidic mouthwash composition, prepared by the method of claim 1, comprising:
    water insoluble flavoring oils in an amount of about 0.1 to about 3.0% by weight of said composition;
    a surfactant that is a hydrogenated castor oil, in an amount of less than about 0.6% by weight of said composition;
    a humectant, in an amount of about 1.0 to about 20.0% by weight of said composition;
    an antimicrobial agent, in an effective amount, that is a combination of cetylpyridinium chloride and domiphen bromide
    wherein the ratio of antimicrobial agent to surfactant in the composition is about 1 part antimicrobial agent to about 1-500 parts surfactant; and
    water, in an amount of about 70 to about 95% by weight of said composition, wherein said composition is a homogeneous, uniform, composition in appearance.

18. The aqueous, non-alcoholic composition of claim 1 wherein said flavor oils are about 0.05 to about 2.0% by weight of said composition.

19. An aqueous slightly acidic non-alcoholic mouthwash composition, prepared by the method of claim 1, consisting of:
    flavoring oils in an amount of about 0.05 to 2.0% by weight of said composition;
    a non-ionic surfactant that is a hydrogenated castor oil, said surfactant present in an amount of less than about 0.5% by weight of said composition;
    a humectant that is glycerin in an amount of about 1.0 to about 20.0% by weight of said composition; and
    an antimicrobial agent that is cetylpyridinium chloride in an amount of about 0.002 to about 0.2% by weight of said composition.

20. The composition of claim 19 wherein said antimicrobial agent additionally includes domiphen bromide at a ratio of 10 to 50 parts CPC to CB.

21. The composition of claim 19 wherein said surfactant is about or less than about 0.45% by weight of said composition.

22. The composition of claim 19 wherein said humectant is about 10% by weight of said composition.

* * * * *